United States Patent
Foerster et al.

(10) Patent No.: US 8,137,381 B2
(45) Date of Patent: Mar. 20, 2012

(54) KNOTLESS SUTURE ANCHOR HAVING DISCRETE POLYMER COMPONENTS AND RELATED METHODS

(75) Inventors: Seth A. Foerster, San Clemente, CA (US); David Aldridge, Laguna Hills, CA (US)

(73) Assignee: ArthroCare Corporation, Austin, TX (US)

( * ) Notice: Subject to any disclaimer, the term of this patent is extended or adjusted under 35 U.S.C. 154(b) by 976 days.

(21) Appl. No.: 12/106,652

(22) Filed: Apr. 21, 2008

(65) Prior Publication Data

US 2008/0319478 A1    Dec. 25, 2008

Related U.S. Application Data

(60) Provisional application No. 60/913,985, filed on Apr. 25, 2007.

(51) Int. Cl.
*A61B 17/04*    (2006.01)
(52) U.S. Cl. .................................................. 606/232
(58) Field of Classification Search .............. 606/103, 606/213, 232, 300; 623/13.13–13.14
See application file for complete search history.

(56) References Cited

U.S. PATENT DOCUMENTS

| | | | |
|---|---|---|---|
| 918,570 A | 4/1909 | Mather | 292/318 |
| 1,153,053 A | 9/1915 | Forster | 43/44.85 |
| 1,565,041 A | 12/1925 | Arneu | 24/129 R |
| 2,269,963 A | 1/1942 | Wrapler | 604/604 |
| 2,485,531 A | 10/1949 | Dzus et al. | 128/92 |
| 2,600,395 A | 6/1952 | Domoj et al. | 87/13 |
| 3,143,916 A | 8/1964 | Rice | 85/71 |
| 3,942,407 A | 3/1976 | Mortensen | 85/71 |
| 3,946,740 A | 3/1976 | Bassett | 128/334 |
| 3,994,521 A | 11/1976 | Van Gompel | 292/319 |
| 4,109,658 A | 8/1978 | Hughes | 128/340 |
| 4,210,148 A | 7/1980 | Stivala | 606/232 |
| 4,274,324 A | 6/1981 | Giannuzzi | 411/38 |
| 4,301,551 A | 11/1981 | Dore et al. | 623/13.3 |
| 4,319,428 A | 3/1982 | Fox | 47/42 |
| 4,345,601 A | 8/1982 | Fukuda | 128/339 |
| 4,373,530 A | 2/1983 | Kilejian | 128/334 R |

(Continued)

FOREIGN PATENT DOCUMENTS

DE    3509417    9/1986

(Continued)

OTHER PUBLICATIONS

PCT Search Report and Written Opinion for PCT/US06/21125 6pgs, Mailed May 22, 2008.

(Continued)

*Primary Examiner* — Melanie Tyson
*Assistant Examiner* — Son Dang
(74) *Attorney, Agent, or Firm* — Matthew Scheele; Brian Szymczak

(57) ABSTRACT

A knotless bone anchor and method for securing soft tissue, such as tendons, to bone, includes a plurality of discrete components. In one variation of the invention, the bone anchor includes a proximal toggle component, an intermediate plug component, and a distal sleeve component. Suture is looped around the plug component and once the anchor is actuated, the suture is compressed between the plug and the sleeve components. Advantageously, one or more of the components may be made of a biocompatible polymer. The polymeric components may be detachably joined to a drive shaft using a plurality of sacrificial fills. The sacrificial fills are broken or severed during deployment of the anchor. Related instruments and methods are also described.

17 Claims, 8 Drawing Sheets

U.S. PATENT DOCUMENTS

| | | | |
|---|---|---|---|
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst | 606/72 |
| 5,258,016 A | 11/1993 | DiPoto et al. | 606/232 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,306,290 A | 4/1994 | Martins et al. | 606/232 |
| 5,324,308 A | 6/1994 | Pierce | 606/232 |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | 606/72 |
| 5,364,407 A | 11/1994 | Poll | 606/139 |
| 5,376,118 A | 12/1994 | Kaplan et al. | 623/23.72 |
| 5,383,905 A | 1/1995 | Gold et al. | 606/232 |
| 5,405,352 A | 4/1995 | Weston | 606/148 |
| 5,405,359 A | 4/1995 | Pierce | 606/232 |
| 5,411,523 A | 5/1995 | Goble | 606/232 |
| 5,413,579 A | 5/1995 | Tom Du | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | DuToit | 606/73 |
| 5,472,452 A | 12/1995 | Trott | 606/232 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,658,313 A | 8/1997 | Thal | 606/232 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | D24/145 |
| 5,681,333 A | 10/1997 | Burkhart et al. | 606/148 |
| 5,681,351 A | 10/1997 | Jamiolkowski | 606/232 |
| 5,683,418 A | 11/1997 | Luscombe et al. | 606/232 |
| 5,683,419 A | 11/1997 | Thai | 606/232 |
| 5,690,649 A | 11/1997 | Li | 606/139 |
| 5,693,060 A | 12/1997 | Martin | 606/148 |
| 5,697,950 A | 12/1997 | Fucci et al. | 606/232 |
| 5,702,397 A * | 12/1997 | Goble et al. | 606/232 |
| 5,702,398 A | 12/1997 | Tarabishy | |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | 606/232 |
| 5,725,529 A | 3/1998 | Nicholson et al. | 606/72 |
| 5,725,541 A | 3/1998 | Anspach, III et al. | 606/151 |
| 5,728,136 A | 3/1998 | Thal | 606/232 |
| 5,733,307 A | 3/1998 | Dinsdale | 606/232 |
| 5,741,281 A | 4/1998 | Martin | 606/148 |
| 5,741,282 A | 4/1998 | Anspach, III et al. | 606/151 |
| 5,766,250 A | 6/1998 | Chervitz et al. | 623/13 |
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |

| Patent No. | Kind | Date | Inventor | Class |
|---|---|---|---|---|
| 5,797,927 | A | 8/1998 | Yoon | 606/144 |
| 5,797,963 | A | 8/1998 | McDevitt | 606/232 |
| 5,810,848 | A | 9/1998 | Hayhurst | 606/144 |
| 5,810,854 | A | 9/1998 | Beach | 606/232 |
| 5,814,052 | A | 9/1998 | Nakao et al. | 606/148 |
| 5,814,071 | A | 9/1998 | McDevitt et al. | 606/232 |
| 5,814,072 | A | 9/1998 | Bonutti | 606/232 |
| 5,843,111 | A | 12/1998 | Vijfvinkel | 606/171 |
| 5,849,004 | A | 12/1998 | Bramlet | 606/232 |
| 5,860,978 | A | 1/1999 | McDevitt | 606/72 |
| 5,860,991 | A | 1/1999 | Klein et al. | 606/144 |
| 5,860,992 | A | 1/1999 | Daniel et al. | 606/145 |
| 5,868,789 | A | 2/1999 | Huebner | 606/232 |
| 5,879,372 | A | 3/1999 | Bartlett | 606/232 |
| 5,882,340 | A | 3/1999 | Yoon | 604/164 |
| 5,885,294 | A | 3/1999 | Pedlick et al. | 606/80 |
| 5,891,168 | A | 4/1999 | Thal | 606/232 |
| 5,893,850 | A | 4/1999 | Cachia | 606/72 |
| 5,902,311 | A | 5/1999 | Andreas et al. | 606/144 |
| 5,904,692 | A | 5/1999 | Steckel et al. | 606/139 |
| 5,911,721 | A | 6/1999 | Nicholson et al. | 606/72 |
| 5,921,994 | A | 7/1999 | Andreas et al. | 606/144 |
| 5,935,107 | A | 8/1999 | Taylor et al. | 604/164 |
| 5,935,129 | A | 8/1999 | Mdevitt | 606/72 |
| 5,941,900 | A | 8/1999 | Bonutti | 606/232 |
| 5,941,901 | A | 8/1999 | Egan | 606/232 |
| 5,944,724 | A | 8/1999 | Lizardi | 606/104 |
| 5,944,739 | A | 8/1999 | Zlock et al. | 606/232 |
| 5,947,982 | A | 9/1999 | Duran | 606/139 |
| 5,948,000 | A | 9/1999 | Larsen et al. | 606/232 |
| 5,948,001 | A | 9/1999 | Larsen | 606/232 |
| 5,948,002 | A | 9/1999 | Bonutti | 606/232 |
| 5,957,953 | A | 9/1999 | DiPoto et al. | 606/232 |
| 5,957,968 | A | 9/1999 | Belden et al. | 607/126 |
| 5,961,530 | A | 10/1999 | Moore et al. | 606/148 |
| 5,961,538 | A | 10/1999 | Pedlick et al. | 606/232 |
| 5,968,044 | A | 10/1999 | Nicholson et al. | 606/72 |
| 5,980,558 | A | 11/1999 | Wiley | 606/232 |
| 5,980,559 | A | 11/1999 | Bonutti | 606/232 |
| 5,984,933 | A | 11/1999 | Yoon | 606/148 |
| 5,993,459 | A | 11/1999 | Larsen | 606/104 |
| 6,001,104 | A | 12/1999 | Benderev et al. | 606/80 |
| 6,001,109 | A | 12/1999 | Kontos | 606/148 |
| 6,007,566 | A | 12/1999 | Wenstrom | 606/232 |
| 6,007,567 | A | 12/1999 | Bonutti | 606/232 |
| 6,010,525 | A | 1/2000 | Bonutti et al. | 606/232 |
| 6,013,083 | A | 1/2000 | Bennett | 606/104 |
| 6,017,346 | A | 1/2000 | Grotz | 606/72 |
| 6,022,360 | A | 2/2000 | Reimels et al. | 606/144 |
| 6,022,373 | A | 2/2000 | Li | 606/232 |
| 6,024,758 | A | 2/2000 | Thal | 606/232 |
| 6,033,430 | A | 3/2000 | Bonutti | 606/232 |
| 6,036,699 | A | 3/2000 | Andreas et al. | 606/139 |
| 6,045,571 | A | 4/2000 | Hill et al. | 606/228 |
| 6,045,572 | A | 4/2000 | Johnson et al. | 606/232 |
| 6,045,573 | A | 4/2000 | Wenstrom et al. | 606/232 |
| 6,045,574 | A | 4/2000 | Thal | 606/232 |
| 6,048,351 | A | 4/2000 | Gordon et al. | 606/144 |
| 6,051,006 | A | 4/2000 | Shluzas et al. | 606/148 |
| 6,053,935 | A | 4/2000 | Brenneman et al. | 606/232 |
| 6,056,773 | A | 5/2000 | Bonutti | 606/232 |
| 6,066,146 | A | 5/2000 | Carroll et al. | 606/148 |
| 6,068,648 | A | 5/2000 | Cole et al. | 606/232 |
| 6,086,608 | A | 7/2000 | Elk et al. | 606/232 |
| 6,096,051 | A | 8/2000 | Kortenbach et al. | 606/144 |
| 6,102,934 | A | 8/2000 | Li | 606/232 |
| 6,117,160 | A | 9/2000 | Bonutti | 606/215 |
| 6,117,161 | A | 9/2000 | Li | 606/232 |
| 6,143,004 | A | 11/2000 | Davis et al. | 606/144 |
| 6,146,386 | A | 11/2000 | Blackman | 606/103 |
| 6,146,406 | A | 11/2000 | Shluzas et al. | 606/232 |
| 6,149,669 | A | 11/2000 | Li | 606/232 |
| 6,156,039 | A | 12/2000 | Thal | 606/72 |
| 6,156,056 | A | 12/2000 | Kearns et al. | 606/232 |
| 6,159,235 | A | 12/2000 | Kim | 606/232 |
| 6,162,537 | A | 12/2000 | Martin et al. | 428/373 |
| 6,171,317 | B1 | 1/2001 | Jackson et al. | 606/148 |
| 6,200,329 | B1 | 3/2001 | Fung et al. | 606/232 |
| 6,200,893 | B1 | 3/2001 | Sneh | 438/685 |
| 6,206,895 | B1 | 3/2001 | Levison | 606/144 |
| 6,217,592 | B1 | 4/2001 | Freda et al. | 606/145 |
| 6,221,107 | B1 | 4/2001 | Steiner et al. | 623/13.14 |
| 6,228,096 | B1 | 5/2001 | Marchand | 606/139 |
| 6,241,736 | B1 | 6/2001 | Sater | 606/104 |
| 6,267,766 | B1 | 7/2001 | Burkhart | 606/72 |
| 6,280,474 | B1 | 8/2001 | Cassidy et al. | 623/16.11 |
| 6,293,961 | B2 | 9/2001 | Schwartz | 606/232 |
| 6,315,781 | B1 | 11/2001 | Reinhardt | 606/108 |
| 6,319,252 | B1 | 11/2001 | McDevitt et al. | 606/60 |
| 6,319,269 | B1 | 11/2001 | Li | 606/232 |
| 6,319,271 | B1 | 11/2001 | Schwartz | 606/232 |
| 6,328,758 | B1 | 12/2001 | Tornier et al. | 606/232 |
| 6,355,053 | B1 | 3/2002 | Li | 606/232 |
| 6,409,743 | B1 | 6/2002 | Fenton | 606/232 |
| 6,432,123 | B2 | 8/2002 | Schwartz et al. | 606/232 |
| 6,436,109 | B1 | 8/2002 | Kontes | 606/148 |
| 6,451,030 | B2 | 9/2002 | Li et al. | 606/139 |
| 6,464,713 | B2 | 10/2002 | Bonutti | 606/232 |
| 6,468,293 | B2 | 10/2002 | Bonutti et al. | 606/232 |
| 6,471,715 | B1 | 10/2002 | Weiss | 606/216 |
| 6,475,230 | B1 | 11/2002 | Bonutti et al. | 606/232 |
| 6,491,714 | B1 | 12/2002 | Bennett | 606/232 |
| 6,517,542 | B1 | 2/2003 | Papay et al. | 606/73 |
| 6,520,980 | B1* | 2/2003 | Foerster | 606/232 |
| 6,524,317 | B1 | 2/2003 | Ritchart et al. | 606/72 |
| 6,527,794 | B1* | 3/2003 | McDevitt et al. | 606/232 |
| 6,540,770 | B1 | 4/2003 | Tornier et al. | 606/232 |
| 6,569,187 | B1 | 5/2003 | Bonutti et al. | 606/232 |
| 6,575,987 | B2 | 6/2003 | Gellman et al. | 606/151 |
| 6,582,453 | B1 | 6/2003 | Tran et al. | 606/232 |
| 6,585,730 | B1* | 7/2003 | Foerster | 606/32 |
| 6,635,073 | B2 | 10/2003 | Bonutti | 606/232 |
| 6,638,279 | B2 | 10/2003 | Bonutti | 606/60 |
| 6,645,227 | B2 | 11/2003 | Fallin et al. | 606/232 |
| 6,648,903 | B1 | 11/2003 | Pierson, III | 606/232 |
| 6,652,561 | B1 | 11/2003 | Tran | 606/232 |
| 6,656,183 | B2 | 12/2003 | Colleran et al. | 606/232 |
| 6,660,008 | B1 | 12/2003 | Foerster et al. | 606/72 |
| 6,660,023 | B2 | 12/2003 | McDevitt et al. | 606/232 |
| 6,679,896 | B2 | 1/2004 | Gellman et al. | 606/148 |
| 6,682,549 | B2 | 1/2004 | Bartlett | 606/232 |
| 6,689,154 | B2 | 2/2004 | Bartlett | 606/232 |
| 6,692,516 | B2 | 2/2004 | West et al. | 606/232 |
| 6,736,829 | B1 | 5/2004 | Li et al. | 606/232 |
| 6,770,076 | B2* | 8/2004 | Foerster | 606/326 |
| 6,780,198 | B1* | 8/2004 | Gregoire et al. | 606/232 |
| 6,855,157 | B2* | 2/2005 | Foerster et al. | 606/232 |
| 6,860,887 | B1 | 3/2005 | Frankie | 606/104 |
| 6,939,379 | B2 | 9/2005 | Sklar | 623/13.14 |
| 6,972,027 | B2 | 12/2005 | Fallin et al. | 606/232 |
| 7,083,638 | B2 | 8/2006 | Foerster | 606/232 |
| 7,087,064 | B1 | 8/2006 | Hyde | 606/142 |
| 7,090,690 | B2* | 8/2006 | Foerster et al. | 606/232 |
| 7,104,999 | B2 | 9/2006 | Overaker | 606/142 |
| 7,150,750 | B2 | 12/2006 | Damarati | 623/17.11 |
| 7,150,757 | B2 | 12/2006 | Fallin et al. | 606/232 |
| 7,247,164 | B1 | 7/2007 | Ritchart et al. | 606/232 |
| 7,329,272 | B2 | 2/2008 | Burkhart et al. | 606/232 |
| 7,556,640 | B2 | 7/2009 | Foerster | 606/232 |
| 7,588,587 | B2 | 9/2009 | Barbieri et al. | 606/232 |
| 7,615,061 | B2 | 11/2009 | White et al. | 606/148 |
| 7,637,926 | B2* | 12/2009 | Foerster et al. | 606/232 |
| 7,674,274 | B2 | 3/2010 | Foerster et al. | 606/232 |
| 7,682,374 | B2 | 3/2010 | Foerster | 606/72 |
| 7,695,494 | B2 | 4/2010 | Foerster | 606/232 |
| 7,837,710 | B2* | 11/2010 | Lombardo et al. | 606/232 |
| 2003/0167062 | A1 | 9/2003 | Gambale | 606/232 |
| 2003/0195563 | A1 | 10/2003 | Foerster | 606/232 |
| 2003/0195564 | A1 | 10/2003 | Tran et al. | 606/232 |
| 2004/0093031 | A1 | 5/2004 | Burkhart et al. | 606/232 |
| 2004/0098050 | A1* | 5/2004 | Foerster et al. | 606/232 |
| 2004/0138706 | A1 | 7/2004 | Abrams et al. | 606/232 |
| 2004/0236336 | A1 | 11/2004 | Foerster et al. | 606/72 |
| 2005/0033364 | A1* | 2/2005 | Gregoire et al. | 606/232 |
| 2005/0080455 | A1 | 4/2005 | Schmieding et al. | 606/232 |

| | | | |
|---|---|---|---|
| 2005/0090827 A1 | 4/2005 | Gedebou | 606/72 |
| 2005/0277986 A1* | 12/2005 | Foerster et al. | 606/232 |
| 2006/0004364 A1 | 1/2006 | Green et al. | 606/72 |
| 2006/0074422 A1* | 4/2006 | Story et al. | 606/72 |
| 2006/0079904 A1 | 4/2006 | Thal | 606/72 |
| 2006/0161159 A1 | 7/2006 | Dreyfuss et al. | 606/72 |
| 2006/0271060 A1 | 11/2006 | Gordon | 606/232 |
| 2006/0271105 A1* | 11/2006 | Foerster et al. | 606/232 |
| 2006/0293710 A1 | 12/2006 | Foerster | 606/72 |
| 2007/0142838 A1 | 6/2007 | Jordan | 606/75 |
| 2008/0015594 A1 | 1/2008 | Ritchart et al. | 606/72 |
| 2008/0051836 A1 | 2/2008 | Foerster et al. | 606/232 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2010/0191283 A1* | 7/2010 | Foerster et al. | 606/228 |

FOREIGN PATENT DOCUMENTS

| | | |
|---|---|---|
| EP | 0 535 906 A2 | 4/1993 |
| EP | 0 571 686 A1 | 12/1993 |
| EP | 0 611 557 A2 | 8/1994 |
| EP | 1 072 234 A2 | 1/2001 |
| EP | 1 072 237 A1 | 1/2001 |
| FR | 2777442 | 10/1999 |
| FR | 2777447 | 10/1999 |
| JP | 2286468 | 11/1990 |
| JP | 8-52154 | 2/1996 |
| JP | 08-206121 | 8/1996 |
| JP | 11-502437 | 3/1999 |
| JP | 2000-225118 | 8/2000 |
| WO | 89/10096 | 11/1989 |
| WO | 91/06247 | 5/1991 |
| WO | 95/06439 | 3/1995 |
| WO | 95/25469 | 9/1995 |
| WO | 96/28118 | 9/1996 |
| WO | 97/20522 | 6/1997 |
| WO | 99/53843 | 10/1999 |
| WO | 99/53844 | 10/1999 |
| WO | 02/21997 | 3/2002 |
| WO | 03/049620 | 6/2003 |

OTHER PUBLICATIONS

PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Examination Report for PCT/US01/17689 15pgs, Feb. 9, 2003.
PCT International Search Report for PCT/US02/17493 1 pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1 pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
UK Search Report for GB 0816111.9 3pgs, Dec. 16, 2008.
PCT Search Report and Written Opinion for PCT/US06/20657 7pgs, Mailed Oct. 2, 2007.
EP Extended Search Report for EP09162639 4pgs, Oct. 28, 2009.
EP Supplementary European Search Report for EP02792506 3pgs, Mar. 24, 2010.
European Search Report for EP 02734649 3pgs, Jan. 22, 2009.

* cited by examiner

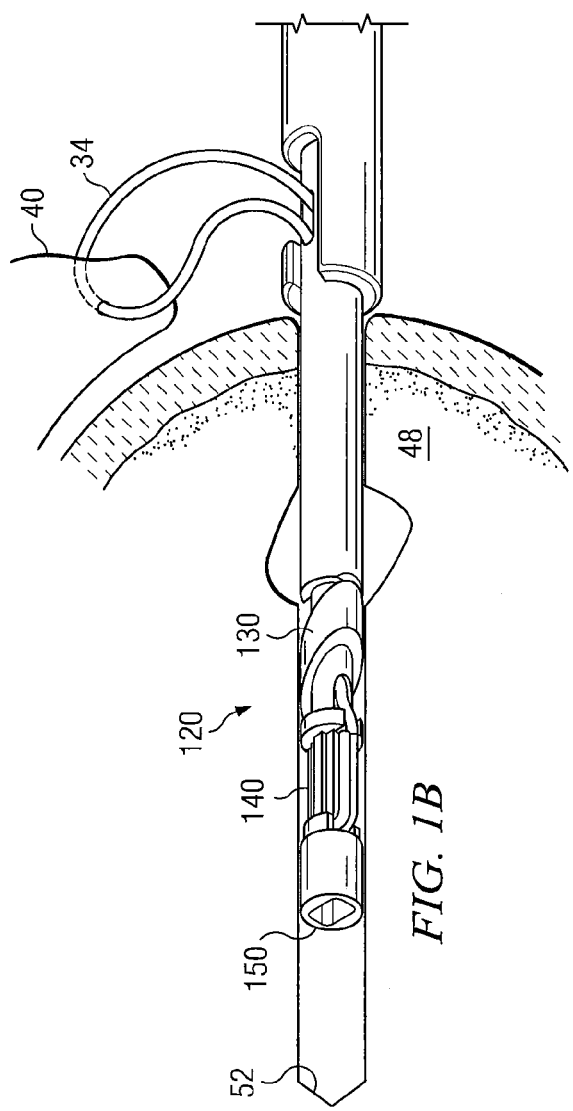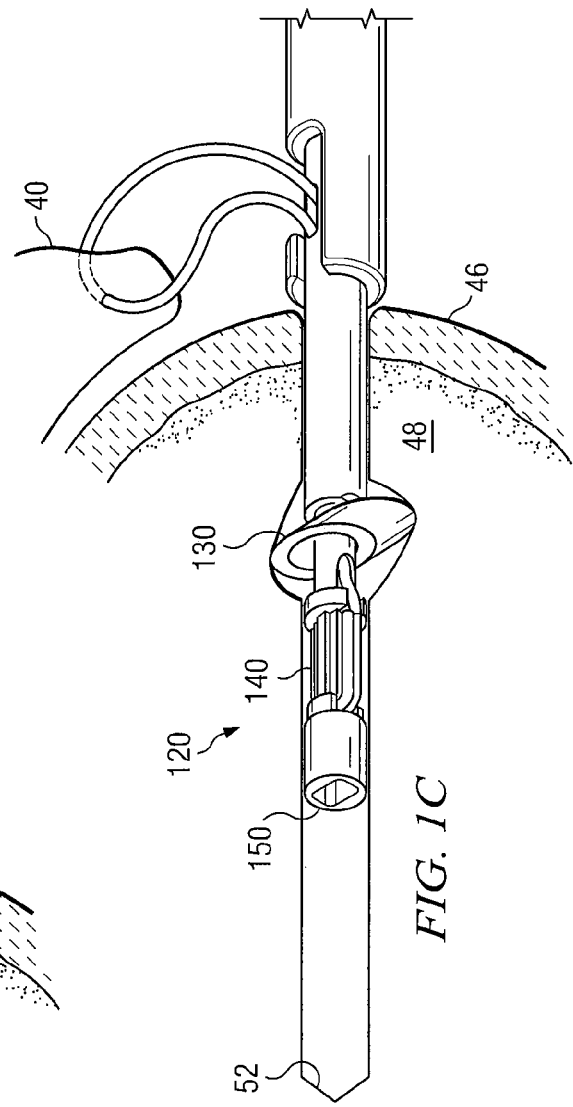

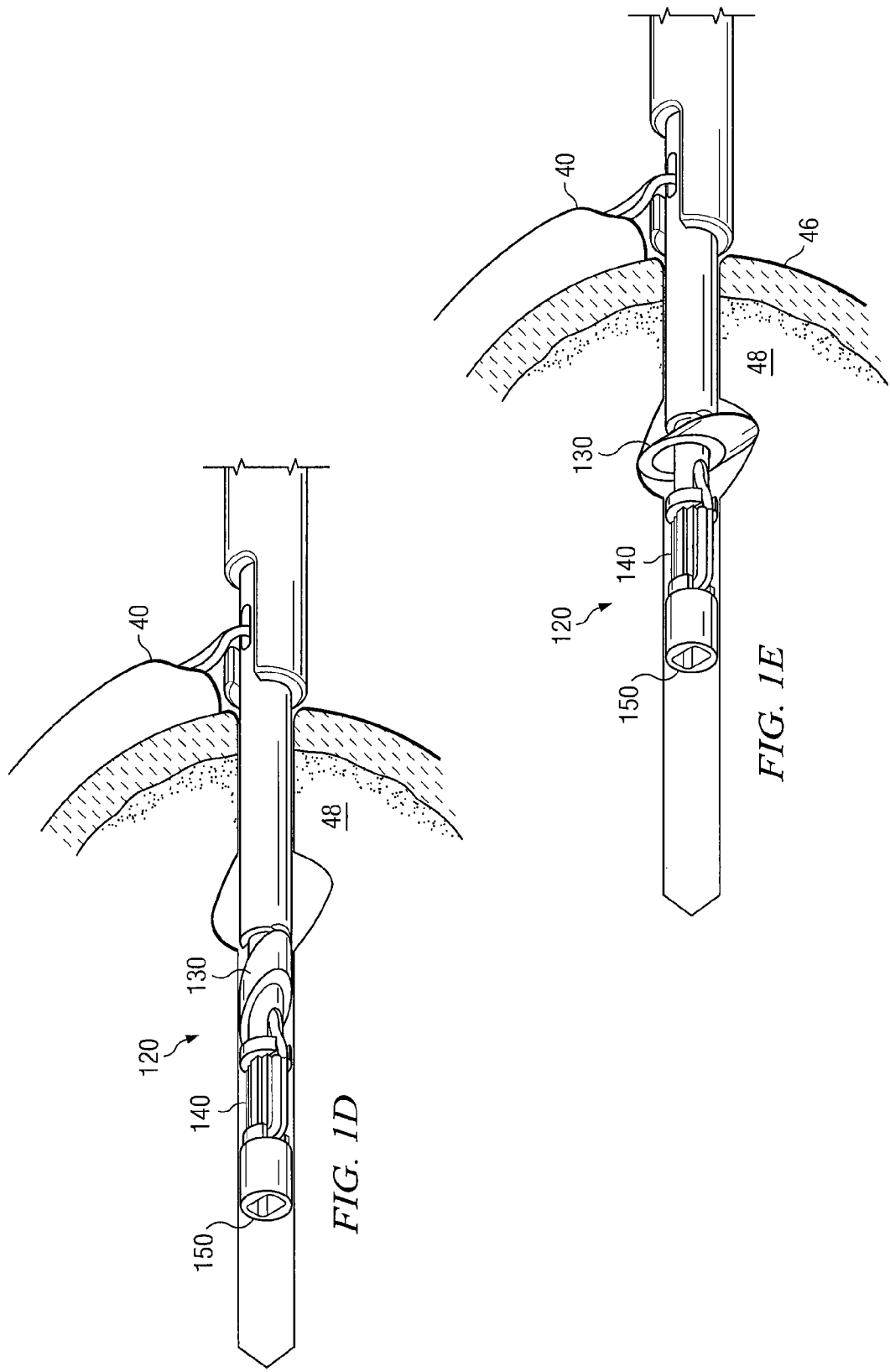

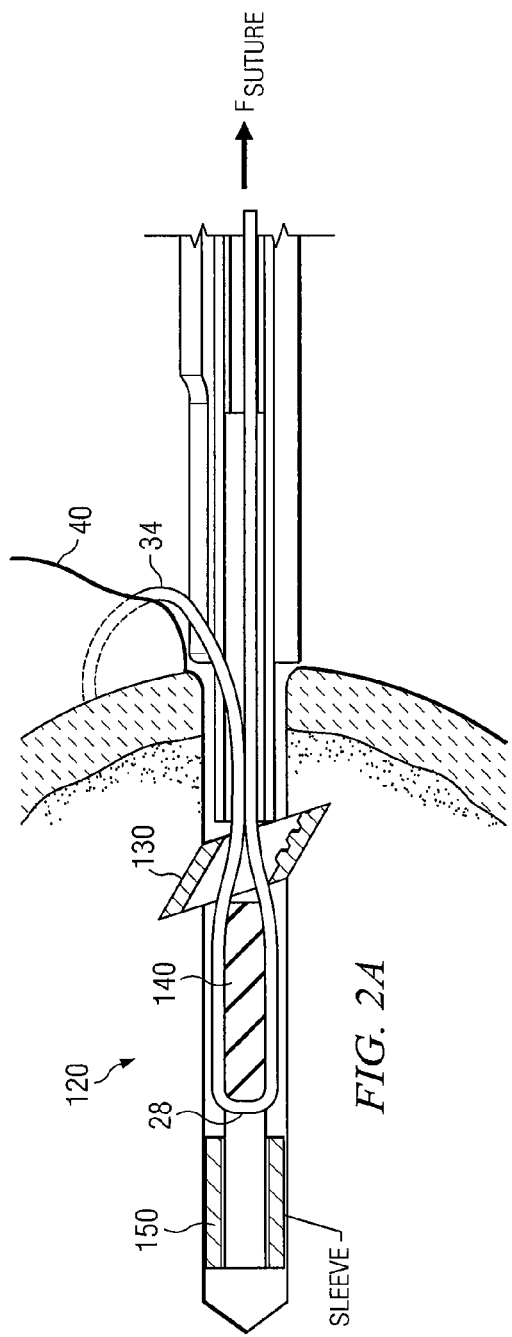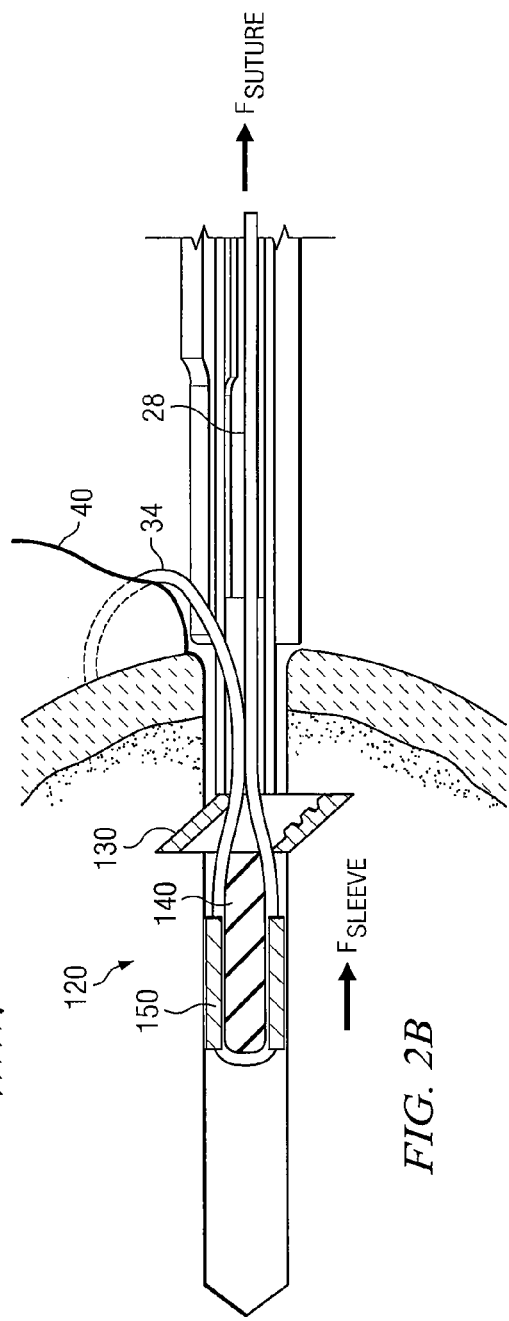

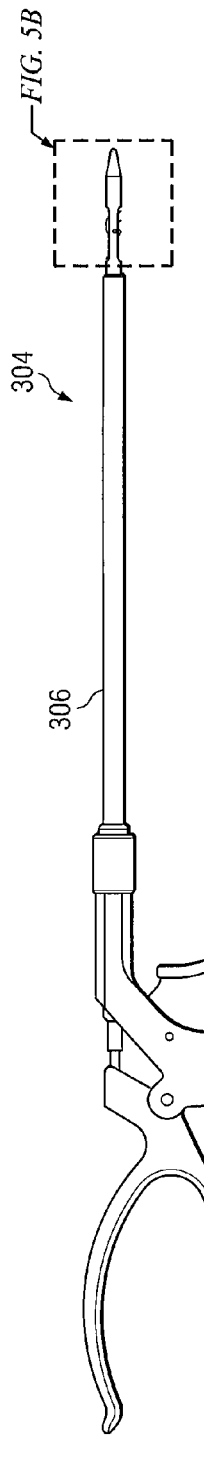
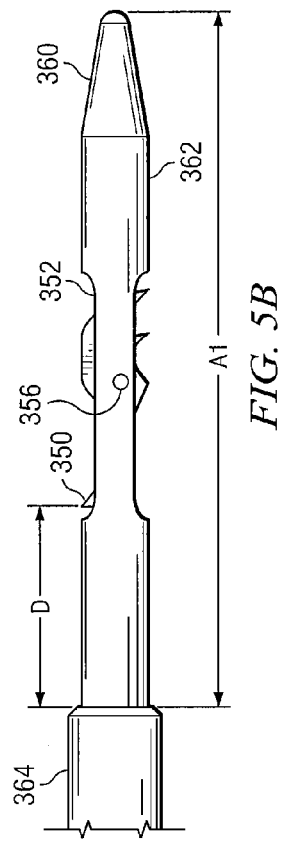
FIG. 5A
FIG. 5B

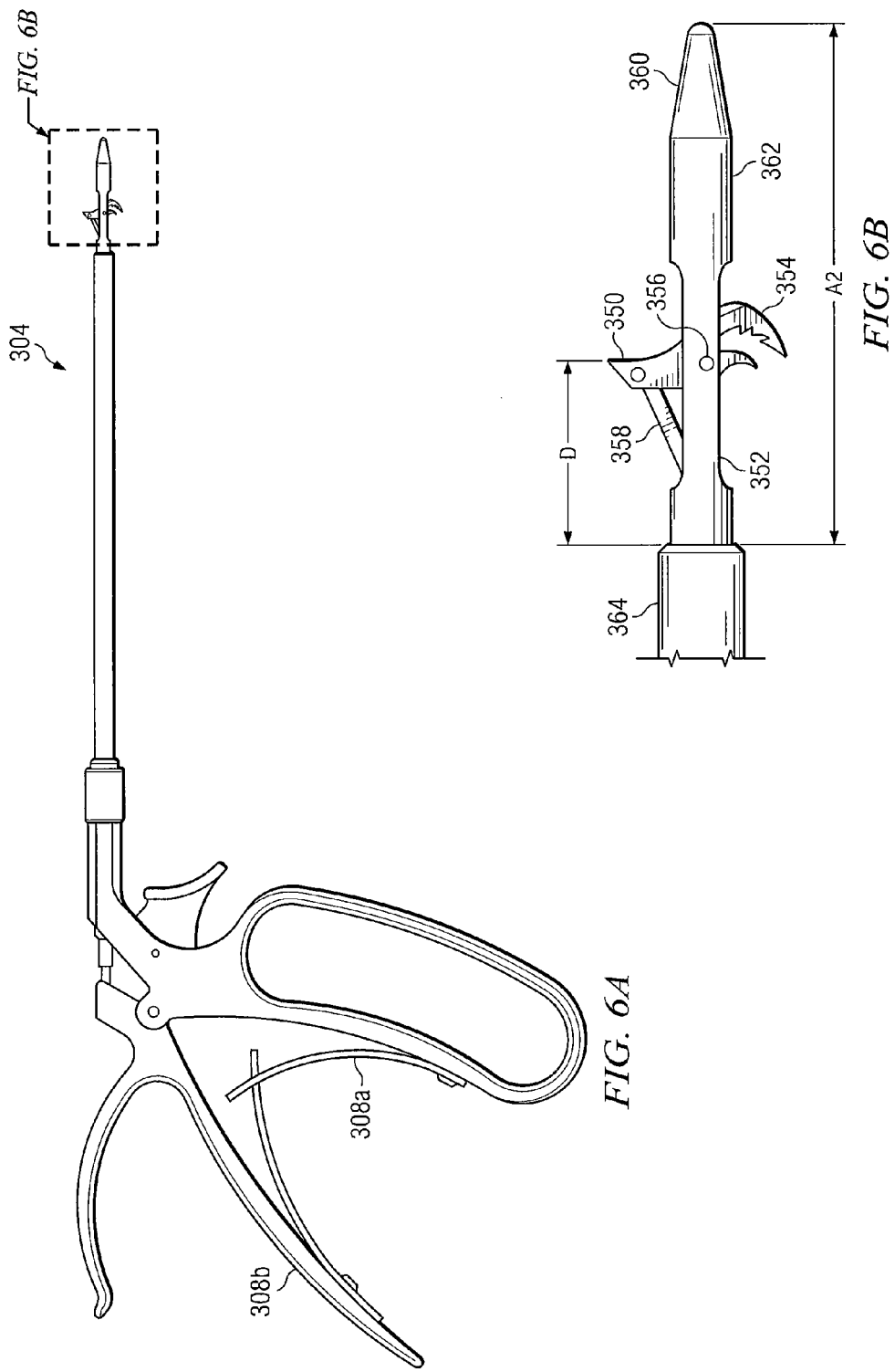

KNOTLESS SUTURE ANCHOR HAVING DISCRETE POLYMER COMPONENTS AND RELATED METHODS

CROSS-REFERENCE TO RELATED APPLICATIONS

This application claims the benefit of U.S. Provisional Patent Application No. 60/913,985 filed Apr. 25, 2007, the complete disclosure of which is incorporated herein by reference for all purposes.

TECHNICAL FIELD OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

BACKGROUND

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

The above described surgical techniques are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Various less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, difficult or impossible to adjust, and are located in less than optimal areas of the shoulder. Suture tension is also impossible to measure and adjust once the knot has been fixed. Much skill is required to both place the sutures in the soft tissues, and to tie knots while working through a trocar under endoscopic visualization.

There have been attempts to solve the problem of placing sutures in soft tissues and tying knots in an endoscopic environment, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrotte the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

Another approach for repairing the rotator cuff or fixing other soft tissues to bone, wherein suture tension can be adjusted, the suture anchor resides completely below the cortical bone surface, and there is no requirement for the surgeon to tie a knot to attach the suture to the bone anchor is disclosed in U.S. Pat. Nos. 6,770,076; 7,083,638; and 6,780,198 assigned to Opus Medical, and now assigned to ArthroCare Corporation. These patents disclose, amongst other things, a knotless anchor system comprising a bone anchor and insertion instrument that affixes an anchor in a bone passageway with a toggling structure, semi-automatically tensions the suture until the tissue is in a desired location, and immobilizes the suture by compressing the suture between various components of the anchor. Despite these patents setting forth various techniques for arthroscopically attaching tissue and generally overcoming many of the shortcomings identified above, enhanced anchoring and deployment systems are still desirable.

A significant number of surgeons prefer that the bone anchors they use in the performance of, for example, a rotator cuff repair be constructed of materials that are non-metallic. This allows for easier post operative imaging using MRI. Also, in the event of a revision to the initial surgery, non metallic anchors are easier to work around or drill through. Therefore, it is desirable, for example, to provide an anchoring system having a robust polymeric suture guide that is capable of holding a suture in place while withstanding the forces imposed on it during suture tensioning; to provide an anchoring system made of a wide variety of materials having varying degrees of strength; to provide an improved insertion instrument that can be conveniently actuated to deploy and detach one or more anchor components from the insertion instrument; and to provide an improved bone preparation instrument that can create spaces for the above described devices.

SUMMARY OF THE INVENTION

One embodiment of the present invention is a bone anchor for attaching tissue to a bone. The anchor has multiple separate or discrete components including a bone affixing component, a suture guide component, and a suture locking component. The bone affixing component serves to hold the anchor in a bone tunnel, the suture guide component serves to hold the suture during tensioning, and the suture locking component serves to immobilize the suture.

In another embodiment of the present invention, the bone affixing component is an oval-shaped disc. The disc has a first, low profile, insertion orientation and a second, radially enlarged, deployed orientation. The enlarged cross section of the deployed orientation securely affixes the anchor in a bone tunnel.

In another embodiment of the present invention, the suture guide component has a plug or bullet shape. The suture is looped around the plug and is held in position along a path by the suture guide. The plug, due to its robust monolithic design, may be made of a polymer or another material known to have less mechanical strength than various metals such as stainless steel. The plug is positioned distal to the affixation structure such that when a suture is tensioned around the plug member, a proximal surface of the plug abuts a distal surface of the bone affixation structure, thus providing a fixed point to which the soft tissues being repaired may be referenced. The plug member around which the suture is passed is immobile relative to the surface of the bone, and provides a means by which the soft tissues may be held in apposition to the bone at a desired tension.

In another embodiment of the present invention, the sleeve component includes an internal cavity or lumen that is sized to accept the plug component therein. The size of the internal lumen or cavity is such that there is a gap between the inner suture guide member and wall of the internal lumen. However, when a suture is present in the suture guide or channel of the plug component, and the sleeve component is positioned coaxially to the plug, the suture is compressed and therefore immobilized by frictional forces developed between the suture limbs, the plug, and the sleeve.

One or more of the components of the bone anchor may be detachably joined to a driver shaft. The anchor components may be joined to the driver shaft by one or more sacrificial fills. The sacrificial fill may be severed or broken to deploy the individual component, and separate the anchor component from the shaft upon actuation of the driver instrument. In one embodiment, an elongate die tube and driver shaft are concentric. The die tube is disposed exteriorly and includes a distal abutment surface. As the inner drive shaft is pulled proximally, one or more of the anchor components abuts the distal end of the die shaft and is forced off the drive shaft. In this manner the sacrificial fills securely hold the anchor on the shaft during insertion and until deployment is desired.

In another embodiment of the present invention, the sacrificial fills are sized differently from one another. The sacrificial fills corresponding to the toggle have a different size than those corresponding to the plug. In one embodiment, the sacrificial fills corresponding to the toggle member include a set of sacrificial fills that are smaller in diameter than a set of sacrificial fills corresponding to the plug member, or the sleeve member.

In another embodiment of the present invention a method for securing a soft tissue to a bone body includes placing a stitch in the soft tissue to obtain at least one free suture end; threading a bone anchor with the free suture end; inserting the anchor into a bone tunnel; actuating a first component of the anchor to affix the anchor in the bone tunnel; tensioning the suture until the tissue is held under tension in a desired location subsequent to the actuating step; and locking the suture wherein the anchor is detached from the drive member by severing the sacrificial fills. The sacrificial fills join the anchor to the drive shaft and may be made of polymer. Additionally, the actuating step may be carried out by toggling the first anchor component. The method may further be limited to attaching specific tissue such as the rotator cuff. The anchor may comprise a suture guide or channel component including a plug-shaped body having an external groove disposed about an exterior surface. The locking step may be carried out by compressing the suture between a plug component and a sleeve component.

In another embodiment of the present invention, a bone tunnel preparation instrument is adapted to undercut a subcortical tissue mass along a bone passageway or socket. The instrument includes a distal end section and a lateral window in the distal end section that houses a punch member. The punch member has at least one cutting edge and is operatively connected to a manual trigger. Upon actuation of the trigger, the cutting edge of the punch protrudes from the window to the extent that the trigger is actuated thereby modifying and cutting out subcortical tissue in the vicinity of the window.

The punch shape in one embodiment includes a trailing cutting edge that is opposite the leading cutting edge and a tissue capture area that engulfs tissue as the punch sweeps out from the window. The punch may be pivotally mounted within the window so as to pivot when it is actuated. In one embodiment of the present invention, the punch sweeps a tissue area matching that of a bone anchor to be deployed in the bone tunnel. In another embodiment, a distance between the cutting leading edge and a fixed stop along the instrument shaft remains constant as the cutting edge sweeps through tissue.

Still other embodiments of the present invention shall become apparent to the reader upon reading the following disclosure with reference to the appended figures.

BRIEF DESCRIPTION OF THE DRAWINGS

FIGS. 1A-1E are partial sectional views illustrating the steps to carry out attaching soft tissue to bone in accordance with one embodiment of the present invention;

FIGS. 2A-2B are enlarged sectional views illustrating locking a suture in an anchor to reattach a rotator cuff tendon;

FIG. 5A is a side view of the bone tunnel preparation instrument in a low profile delivery or insertion configuration;

FIG. 5B is an enlarged view of the distal end section of the instrument shown in FIG. 5A;

FIG. 6A is a side view of the bone tunnel preparation instrument in a large profile or actuated configuration;

FIG. 6B is an enlarged view of the distal end section of the instrument shown in FIG. 6A.

DETAILED DESCRIPTION

The present invention provides an improved knotless suture anchor apparatus for anchoring a length of suture with respect to a body cavity. In the exemplary embodiment described herein, the apparatus is used to anchor a length of suture to a bone structure, for example, the humeral bone of the human shoulder. The length of suture is desirably looped through soft tissue, such as a rotator cuff tendon, to approximate and fix the soft tissue with respect to the body cavity (e.g., bone structure). It should be understood, however, that the suture anchor apparatus may be utilized to secure a length of suture to body cavities other than in a bone structure, and may even be used to anchor the suture outside of a body cavity, merely to a predetermined location within the body. In this regard, the preferred apparatus includes one or more anchor components within which the length of suture may be anchored without knots. The anchor also includes one or more components or structures to affix the anchor in a bone passageway.

As mentioned herein, the present invention is particularly well-suited for repairing rotator cuff injuries by re-attaching the rotator cuff tendon to the outside of the humeral head. The invention permits minimally invasive surgeries on such injuries and greatly facilitates rapid and secure fixation of the rotator cuff tendon to the humeral head. It should be understood that the same principles described herein apply to the repair of other injuries in which soft tissue is to be re-attached to a bone structure.

Figure 1A:
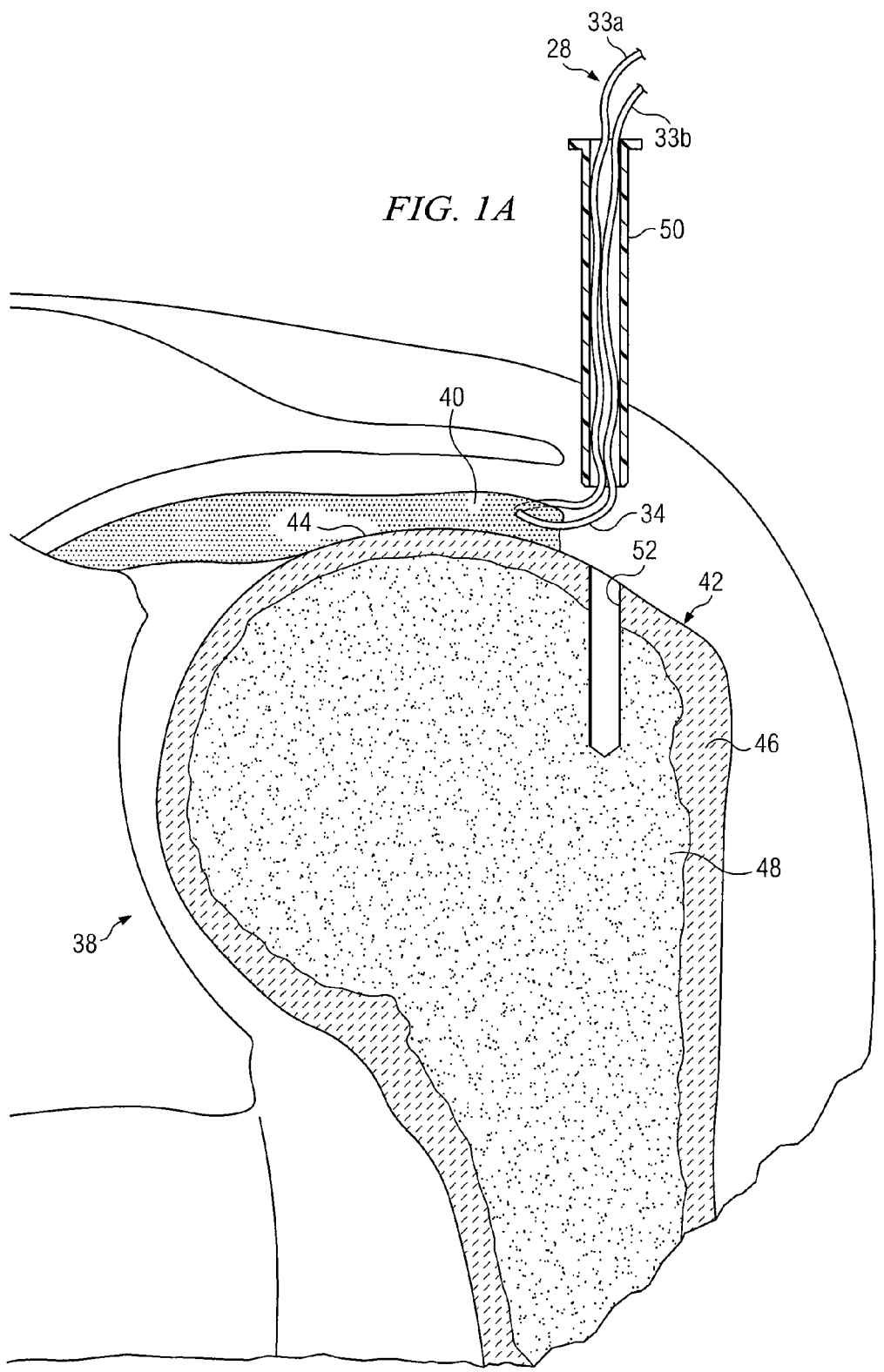

FIGS. 1A-1E show a procedure for repairing a rotator cuff tendon injury in accordance with the present invention. Referring first to FIG. 1A, a partial cross-sectional view through the left shoulder of a human as viewed from the front is illustrated. The rotator cuff tendon 40 is shown in its natural position overlying the bulbous humeral head 42 of the humerus bone. In rotator cuff injuries, the tendon 40 partially or completely separates from its attachment point to the humeral head 42, which point of attachment is typically located along an angled shelf, the greater tuberosity. In minimally invasive surgeries to repair the rotator cuff injury, the surgeon threads one or more sutures 28 through the rotator cuff tendon 40 and anchors them to the greater tuberosity. The suture anchor system, as will be described below, facilitates this latter step of anchoring the sutures to the greater tuberosity.

FIG. 1A shows a generally tubular trocar 50 that provides a conduit through the soft tissue of the shoulder. Typically, the surgeon makes an incision or stab wound through the outer dermal layers of sufficient size to permit passage of the trocar 50 through the skin and the deltoid muscle into proximity with the humeral head 42. Various trocars and techniques for creating the approach passageway are known and may be utilized with the present invention. In addition, more than one incision and conduit may be necessary to perform the several suturing and anchoring steps.

After establishing one or more direct conduits to the humeral head 42, the surgeon passes a length of suture through the soft tissue of the rotator cuff tendon 40 so that a loop 34 of suture material is embedded therein, as seen in FIG. 1A. The two free ends 33a, 33b of the length of suture are withdrawn from the patient and coupled to a suture anchor system. The anchor may be threaded with the suture 28 by hand, with a tool, or perhaps with a snare or wire loop as described in U.S. Pat. No. 6,780,198 the entirety of which is incorporated by reference.

FIG. 1B shows a suture anchor 120 inserted in the bone tunnel or cavity 52. Next, as shown in FIG. 1C, the anchor is affixed to the bone using an anchoring structure or component 130 located on the proximal end of the suture anchor 120. The anchoring structure 130 functions as a toggle member, and rotates from a low profile insertion position to a radially enlarged deployed position. The anchoring component 130 is deployed distal to the hard cortical bone layer 46. In this manner, the suture anchor 120 is prevented from being removed from the tunnel 52 once the anchoring structure 130 is deployed. Although the present invention illustrates a particular anchoring structure 130, any similar expedient will work. Examples of other suitable anchoring structures include those shown in U.S. Pat. Nos. 6,770,076 and 6,582,453, the disclosures of which are hereby incorporated by reference in their entirety. Alternatively, an anchoring structure that expands into contact with or is screwed into the cancellous matter 48 may be used. In short, the present invention includes various anchoring structures except where expressly excluded in the appended claims.

FIG. 1D shows the anchoring system in an unlocked position subsequent to tension being applied to the suture. Tensioning of the tissue may be carried out by hand by simply pulling on the sutures or, more preferably, with a semiautomatic or tensioning mechanism as described in U.S. Pat. No. 6,780,198 the disclosure of which is hereby incorporated by reference in its entirety. In this manner, the suture may be tensioned until the tissue is positioned in a target location.

FIG. 1E shows the step of locking or immobilizing the suture between two components of the anchor without the use of knots. In particular, the suture is compressed between plug 140 and sleeve 150. Locking the suture between multiple components is also described in U.S. Pat. No. 7,083,638 the disclosure of which is hereby incorporated by reference in its entirety.

Although not shown, the remaining steps in the procedure involve withdrawing the instruments from the surgical site and severing the free ends 33a, 33b close to the suture anchor.

FIGS. 2A-2B illustrate additional details of the suture anchor 120 in operation. In particular, FIG. 2A illustrates the anchor 120 affixed in a bone tunnel subsequent to the suture 28 being tensioned with a force $F_{suture}$. The tissue 40 is positioned at a desired location adjacent the bone body. FIG. 2B illustrates the anchor 120 affixed in the bone tunnel subsequent to locking the suture between plug 140 and sleeve 150. In this embodiment of the present invention, the suture extends along a suture guide on an exterior surface of the plug 140, across a distal surface of the plug 140, and returns in the proximal direction to exit the anchor and the bone tunnel. Sleeve 150 is shown as a tubular shaped component having a lumen or cavity that is adapted to receive the plug. A small gap exists between the exterior surface of the plug and the interior surface of the cavity or sleeve such that there is no interference or compression fit between the plug and the sleeve. The gap is less than the thickness of the suture(s) so that the suture is squeezed when the sleeve is urged or pulled over the plug. Indeed, the suture becomes immobilized or locked once the sleeve surrounds the plug. This permanently attaches tissue 40 to the bone.

Although FIGS. 2A-2B show a particular design, the shapes of the anchor components may vary. The plug 140 may have, for example, a bullet shape, cylindrical, spherical, elongate, tapering, or solid shape. Preferably the plug is substantially robust so as to serve at least two functions 1) provide enough force to squeeze and lock the suture, and 2) provide a suture guide that can withstand forces arising from the above mentioned tensioning step. Additionally, although a simple pin, pulley or cross bar may be sufficient when the plug is made of a metal, a more robust shape such as that shown in FIGS. 2A-2B is preferred for materials having less strength such as certain polymers including for example polyetheretherketone (PEEK). Other biocompatible, bioabsorbable or bioactive materials may be incorporated into the design as well.

Figure 3A:
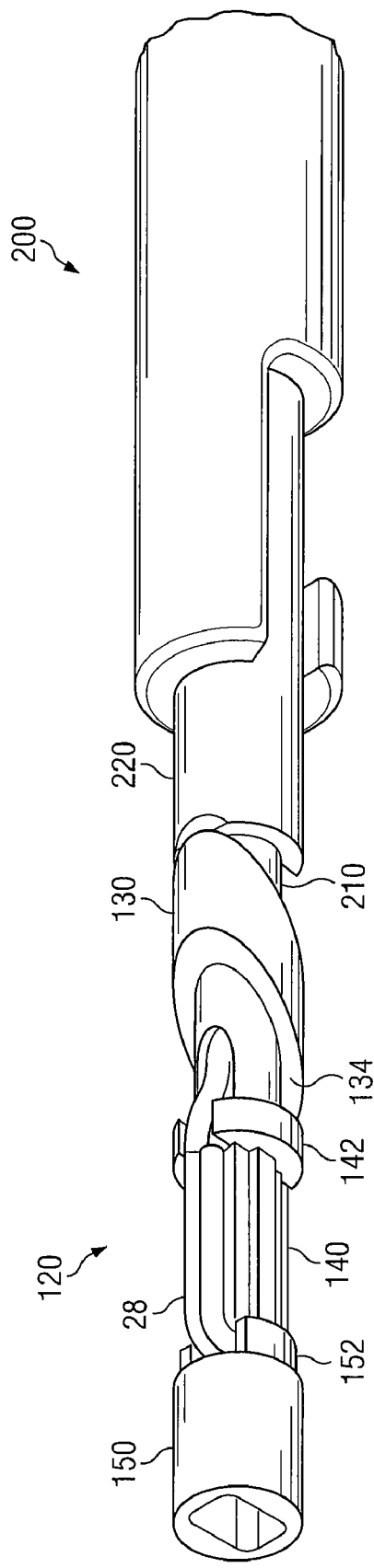
FIG. 3A is a partial perspective view of an anchor positioned on a distal end of a delivery instrument in accordance with the present invention.

FIG. 3A shows an enlarged perspective partial view of an undeployed anchor 120, suture 28, and distal end section of a driver 200. Each of the components of the anchor are shown connected to drive shaft 210. In particular, toggle member 130 is proximal to plug 140. Plug 140 is proximal to sleeve 150. Additionally, a space is present between each of the components such that the anchor components are separated, disconnected, or, in a sense, "free floating". But for the drive shaft 210 and the anchor's detachable connection to the drive shaft as shall be explained in more detail below, the anchor components would be unconstrained and allowed to fall out of position.

In one embodiment of the present invention, as described above, the anchor is affixed in the bone. To this end, an anchoring component such as toggle 130 is moved perpendicular to the longitudinal axis of the shaft. This deployment may be achieved by providing relative opposite motion between drive shaft 210 and driver die 220 such that the die surface forces the toggle to rotate to a transverse direction.

Though not fully shown in these Figures, the driver preferably includes a handle, elongate shaft, and actuation lever or trigger. The actuator member serves to deploy the bone affixing structure, tension the suture, and/or lock the suture in place. An example of a driver instrument is illustrated in U.S. Pat. No. 6,780,198 which is incorporated by reference in its entirety.

Figure 3B:
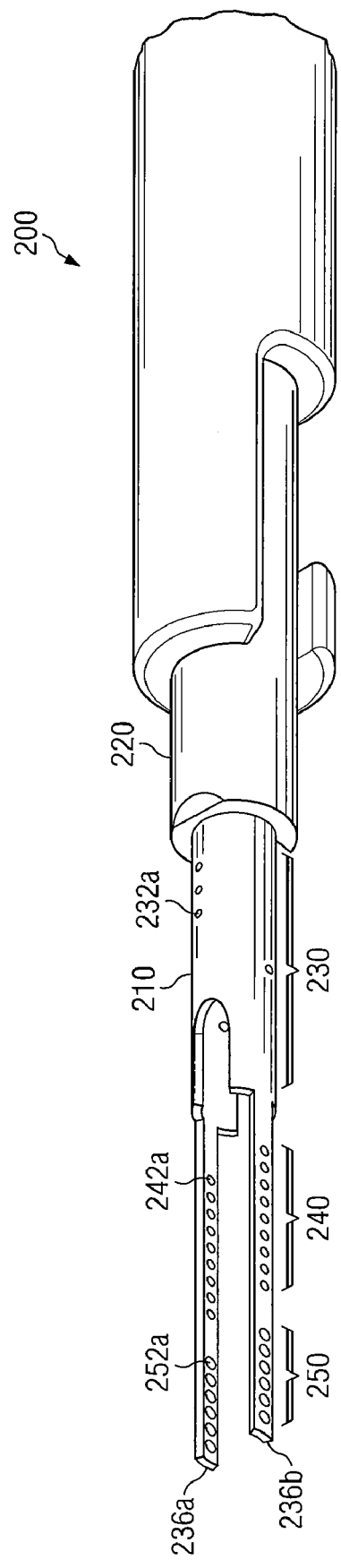
FIG. 3B is a partial perspective view of the distal end of the delivery instrument shown in FIG. 3A excluding the anchor.

FIG. 3B shows an example of a distal end section of a driver instrument 200. Driver shaft 210 is shown having a generally tubular shape and terminating in two arms or ribbons 236a,b, that extend longitudinally. A plurality of holes are arranged on the driver shaft including toggle holes, plug holes, and sleeve holes. Each hole accepts, receives, or is filled with a sacrificial fill or link extending from the anchor. A purpose of the sacrificial fills is to securely hold the anchor components on the shaft until the surgeon desires to actuate and deploy the components. When the surgeon desires to actuate and detach the components from the shaft, relative motion between the drive shaft and the driver die 220 causes the distal surface of the die to push the anchor off the drive shaft. The sacrificial fills shear or break as the drive die 220 pushes the anchor 120. As discussed further below, the sacrificial fills may be designed to control the order in which the anchor components are actuated (or detached). Additionally, the anchor and sacrificial fills may be conveniently inserted molded onto the shaft so that the anchor is formed on the shaft and the plurality of holes are filled with molten polymer. When the polymer solidifies, the sacrificial fills are created.

FIG. 3B shows the holes increasing in diameter along the length of the driver shaft. This design encourages the most proximal fills to break first, and to encourage the more distal fills along the length of the driver ribbons 236a,b to break last. In particular, the sleeve holes 252 have a larger diameter than the plug holes 242, and the toggle holes 232. Similarly, sleeve holes have a progression of increased diameter. Selection of the diameter, location, shape, and number of holes affects the holding strength of the anchor component to the drive shaft. In this embodiment, the anchor affixation or toggle member is actuated and detached from the shaft first. The toggle holes 232 are less numerous and may be smaller than the other fill holes. The sleeve holes 252a are the largest and require the most force to break. The sleeve therefore is the last anchor component to be detached or break from the shaft 210. This sequence is desired because the suture locking step is the final step.

Walking through the sequence of operation again, and referring to FIGS. 3A-3B, when the delivery system pulls on the driver tube 210, the toggle 130 is forced against the driver die 220, breaking the attachments created by the holes 232 and turning the toggle perpendicular to the axis of the anchor. The suture is then tightened, and when the user is satisfied with the suture tension and is ready to lock the suture 28 in place, the delivery system then urges the driver 210 further proximal. A flange 142 abuts the lower (distal) surface 134 of the toggle 130, which places the bonds created between plug holes 242 and the plug 140 in shear. The sacrificial fills break, freeing the plug 140 from the driver ribbons 236, and allow the sleeve 150 to begin to travel proximally as well. The sleeve 150 slides up over the plug 140, trapping the suture in place. When tabs 152 on the sleeve 150 abut the flange 142 on the plug 140, the sacrificial fills or bonds formed between the sleeve holes 252 and the sleeve 150 are placed in shear. The bonds break, allowing the driver ribbons 236a,b to be withdrawn from the bone anchor 120, completing the deployment.

Once deployed, the free floating components are held or bound together by virtue of the suture, extending from the anchor, looping through the tissue, and returning to the anchor. The tension on the suture holds the components together and against the cortical bone shelf. In this manner, this multi-component embodiment provides an elegant solution for attaching tissue to bone.

Figure 4A:
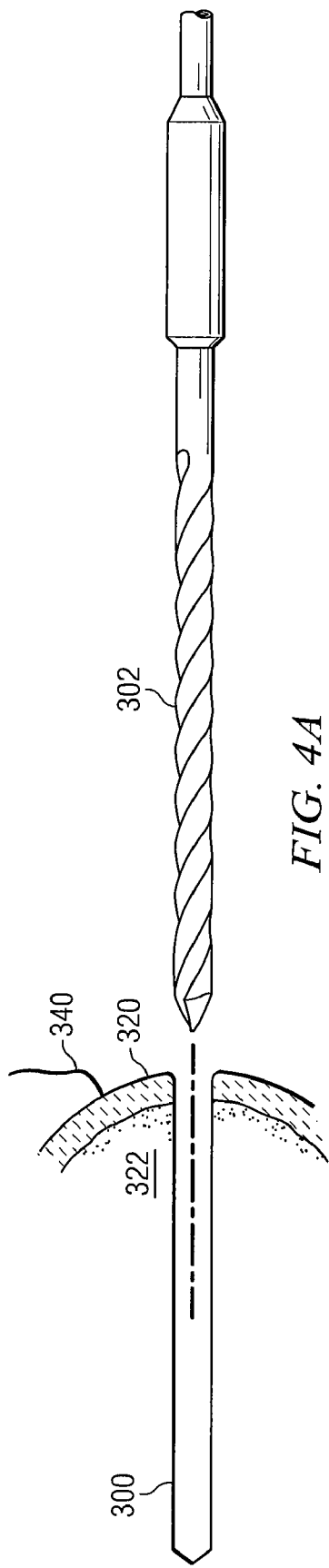
FIGS. 4A-4C are partial sectional views illustrating the steps to carry out preparation of a bone passage or tunnel using a punch instrument in accordance with one embodiment of the present invention.
Figure 4C:
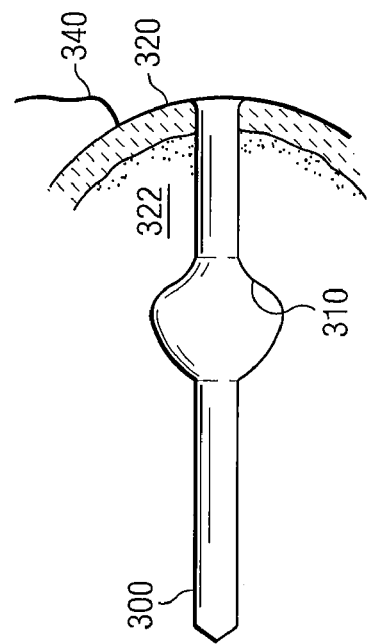
Figure 4B:
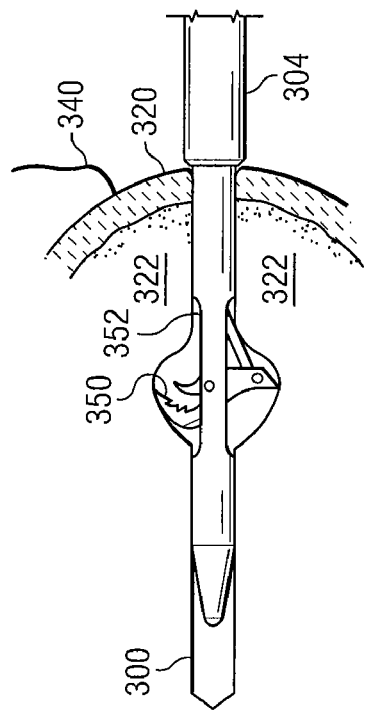

FIGS. 4A-4C show another embodiment of the present invention comprising preparing a bone tunnel 300 for accepting an expanding anchor (not shown). In particular, an enlarged subcortical space 310 is created in this embodiment along the bone tunnel or cavity. Referring first to FIG. 4A, a tunnel 300 is created using a drill, punch, or another instrument 302.

Next, an undercut tool or punch 304 is inserted into the bone tunnel 300 and gradually actuated to modify and create a radially enlarged space 310 in a subcortical layer of bone 322. As shown in FIG. 4B, a cutting edge 350 extends from a window 352 of the punch 304 to carve out, cut, or capture tissue.

FIG. 4C shows the enlarged subcortical space 310 with the undercut punch 304 removed. The enlarged subcortical space 310 is intended to mimic the shape of the volume that is swept or created by the toggle component, described above, during the bone anchor deployment. The creation of an enlarged subcortical space along the bone tunnel is particularly useful when anchors are to be deployed that have a relatively weak, atraumatic, brittle, or flexible bone affixation structure (e.g., toggle ring) because such structures may not consistently or reliably displace bone tissue and achieve a suitable bone lock. It is thus desirable to pre-treat the tunnel and create a subcortical space to receive the bone-affixation structure (e.g., a toggle) such that the anchor may safely lock.

FIGS. 5A-5B show a side view of an undercut punch 304 in a low profile (or insertion) mode. Punch 304 is shown having an elongate shaft 306 connected to a handle 308a. A trigger or actuator 308b is joined to the handle to cause the recessed blade 350 to extend beyond the window and sweep or capture tissue. FIG. 5B is an enlarged view of the distal section of the elongate shaft 306. In particular, distal section includes an inner drive shaft 362, a die shaft 364, and a blade 350 recessed in a window 352. The blade or punch rotates about a pin 356 as the trigger is actuated. Additionally, the punch includes a tip 360 shown at a first distance A1 from the end of the drive die 364. The tip is shown having a rounded, atraumatic end. Additionally, the leading edge of blade 350 is spaced D from the drive die.

FIGS. 6A-6B show a side view of the undercut punch 304 after it has been actuated. In particular, actuation member 308b is shown compressed or manipulated towards handle 308a. This relative motion between the handle and trigger urges the inner drive shaft 362, and tip 360 proximally such that distance A2 is less than A1.

A link member 358 pivotally connects to blade 350 and holds the blade a fixed distance D from the drive die 364. The blade leading edge 350 thus tends to move laterally during its travel and not longitudinally. This substantially lateral or transverse sweep ensures that the blade's sweep mimics the path of the anchor's toggle component, described above.

Additionally, the trailing edge 354 pivots in a direction opposite to the leading edge 350. The trailing edge is shown having a tissue capturing area as well as a plurality of teeth. It is to be understood that the blade may comprise a number of blade surfaces, tissue capture areas, teeth, and other features to sweep tissue and prepare the tunnel for accepting a bone anchor device.

Accordingly, although an exemplary embodiment of the invention has been shown and described, it is to be understood that all the terms used herein are descriptive rather than limiting, and that many changes, modifications, combinations, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A knotless suture anchor for securing soft tissue to bone comprising:
   a first component adapted to affix the anchor in a bone tunnel;
   a second component distal to said first component, said second component comprising a body, an exterior surface, a suture guide disposed on the exterior surface, and a proximal abutment surface adapted to abut a distal surface of said first component, wherein a suture may be looped around the second component and held in position by the suture guide;
   a third component distal to said second component, said third component comprising a cavity and a proximal opening, said cavity being adapted to accept said second component and to compress said suture when the second component is within the cavity of the third component thereby locking the suture in place and wherein said second component is made of a polymer and wherein each of the first component, the second component, and the third component are discrete components.

2. The anchor of claim 1 wherein said first component has a first position and a second position different than said first position, said second position having a larger radial profile than said first position.

3. The anchor of claim 2 wherein said first component has an annular shape.

4. The anchor of claim 1 wherein said suture guide comprises a groove, and a portion of said groove extends across a distal surface of said second component.

5. The anchor of claim 1 wherein each of said first, second, and third components are separate members.

6. The anchor of claim 1 wherein said polymer is PEEK.

7. The anchor of claim 1 wherein each of said first, second and third components are made of an injection molded polymer.

8. The anchor of claim 7 wherein each of said first, second, and third components are detachably formed onto a driver shaft prior to deployment of the anchor, and a first axial space is present between the first and second components and a second axial space is present between the second and third components.

9. The anchor of claim 1 wherein said third component has a sleeve or tubular shape.

10. The anchor of claim 7 wherein each of the components is insert molded onto a drive shaft.

11. A suture anchor for affixing tissue to bone comprising:
a toggle member that is movable from a low profile insertion position to a large profile position wherein said large profile position provides said suture anchor a large diameter section that affixes said anchor in a bone tunnel;
a plug member comprising an external surface such that a suture may be looped around said plug; and
a sleeve member having an internal lumen that may receive said plug and compress a suture between said plug and said sleeve to lock said suture in place and wherein each of said toggle member, plug and sleeve member are discrete components.

12. The suture anchor of claim 11 wherein said plug member is detachably connected to a shaft member by at least one plug sacrificial fill.

13. The suture anchor of claim 11 wherein said sleeve member is detachably connected to a shaft member by at least one sleeve sacrificial fill.

14. The suture anchor of claim 11 wherein said toggle member is detachably connected to a shaft member by at least one toggle sacrificial fill.

15. The suture anchor of claim 11 wherein said toggle member comprises a disc shape.

16. A kit comprising:
an anchor as recited in claim 1;
an elongate member having a distal section upon which said anchor is detachably connected; and
a handheld tunnel preparation instrument comprising a handle, an elongate shaft, and an actuatable punch housed within said distal end section of said elongate shaft.

17. A knotless suture anchor for securing soft tissue to bone comprising:
a first component adapted to affix the anchor in a bone tunnel;
a second component distal to said first component, said second component comprising a suture guide, and a proximal abutment surface adapted to abut a distal surface of said first component;
a third component distal to said second component, said third component comprising a cavity and a proximal opening, said cavity being adapted to accept said second component and to compress a suture when the second component is within the cavity of the third component thereby locking the suture in place and wherein said second component is made of a polymer; and
wherein said second component comprises a body and exterior surface, and said suture guide comprises a groove disposed about the exterior surface, and a portion of said groove extends across a distal surface of said second component.

* * * * *